United States Patent
Rheinberger et al.

(10) Patent No.: US 8,222,315 B2
(45) Date of Patent: Jul. 17, 2012

(54) METHOD FOR PRODUCING COMPOSITES THAT CAN BE USED IN DENTISTRY

(75) Inventors: Volker Rheinberger, Vaduz (LI); Konrad Hagenbuch, Grabs (CH); Petra Dellafior, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 65 days.

(21) Appl. No.: 12/084,735

(22) PCT Filed: Nov. 9, 2006

(86) PCT No.: PCT/EP2006/068310
§ 371 (c)(1),
(2), (4) Date: May 9, 2008

(87) PCT Pub. No.: WO2007/054547
PCT Pub. Date: May 18, 2007

(65) Prior Publication Data
US 2009/0234044 A1    Sep. 17, 2009

(30) Foreign Application Priority Data

Nov. 11, 2005 (DE) .......................... 10 2005 053 954

(51) Int. Cl.
*A61F 2/00* (2006.01)
*A61L 24/00* (2006.01)
*A61K 6/083* (2006.01)
*C08F 2/00* (2006.01)
*C08F 265/04* (2006.01)
*C08F 267/06* (2006.01)

(52) U.S. Cl. .......... 523/115; 523/113; 526/75; 525/304; 525/302

(58) Field of Classification Search .................. 523/109, 523/113, 115, 116, 118; 526/75; 525/244, 525/302, 304
See application file for complete search history.

(56) References Cited

U.S. PATENT DOCUMENTS

| | | |
|---|---|---|
| 2,013,295 A | 9/1935 | Tidd |
| 4,920,188 A * | 4/1990 | Sakashita et al. ............. 526/196 |
| 4,937,144 A | 6/1990 | Podszun et al. |
| 4,946,901 A | 8/1990 | Lechner et al. |
| 6,139,322 A * | 10/2000 | Liu ............................ 433/199.1 |
| 6,281,271 B1 * | 8/2001 | Rumphorst et al. .......... 523/211 |

FOREIGN PATENT DOCUMENTS

| | | |
|---|---|---|
| DE | 2 000 771 | 7/1970 |
| DE | 30 00 213 | 7/1981 |
| DE | 0 674 896 | 10/1995 |
| DE | 102005053954 | 5/2007 |
| EP | 0 270 915 | 6/1988 |
| EP | 1 502 571 | 2/2005 |
| WO | 98/48766 | 11/1998 |
| WO | 2004/058193 | 7/2004 |

OTHER PUBLICATIONS

Micromeritics Instrument Corporation Particle Characterization, 2007, http://www.azom.com/Details.asp?ArticleID=3763.*

* cited by examiner

*Primary Examiner* — Liam Heincer
(74) *Attorney, Agent, or Firm* — Ann M. Knab; Thad McMurray

(57) ABSTRACT

The present invention relates to a process for the preparation of composites which can be used in the dental field, in which
a) mono- or polyfunctional monomers dissolved in a solvent are polymerized to give a polymer gel thoroughly swollen with the solvent,
b) the polymer gel produced is subjected to preliminary size reduction,
c) a reactive gel is subsequently prepared by the polymer gel, subjected to preliminary size reduction, incorporating a polymerizable monomer or a mixture of polymerizable monomers in the polymer gel while simultaneously removing the solvent, and
d) a dental composite is prepared from the reactive gel thus obtained.

20 Claims, 1 Drawing Sheet

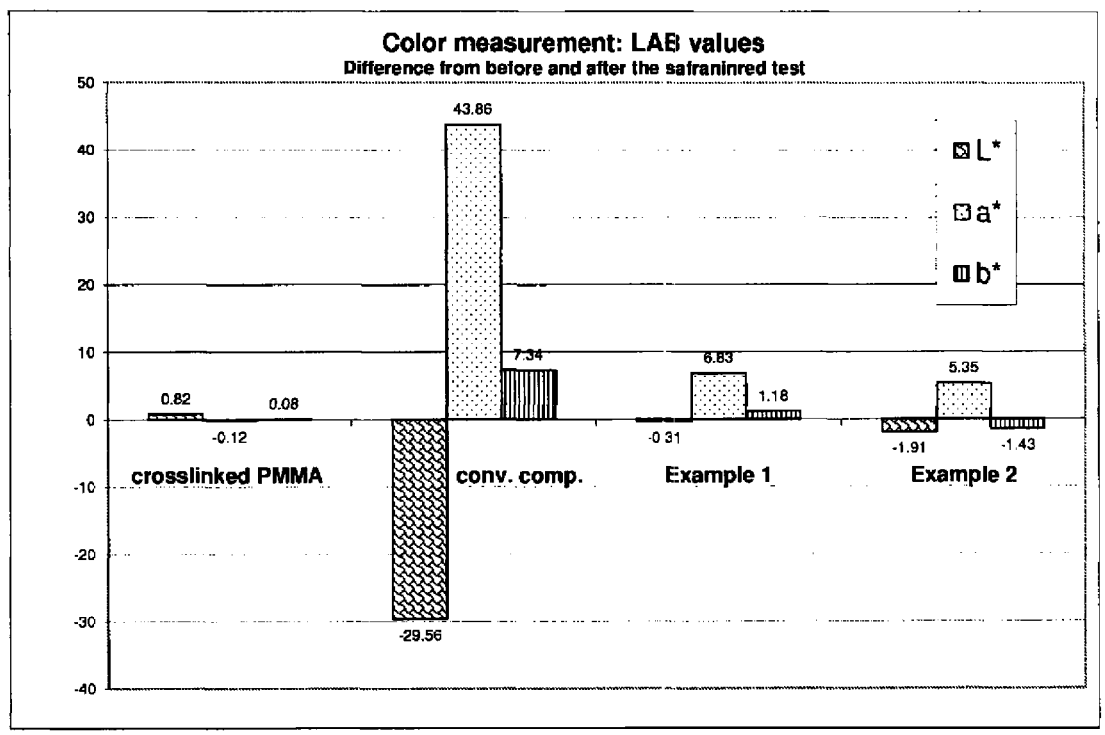

METHOD FOR PRODUCING COMPOSITES THAT CAN BE USED IN DENTISTRY

This application claims the priority of DE 10 2005 053 954.8-42.

The present invention relates to a process for the preparation of composites which can be used in the dental field, to the composites prepared according to this process as such and to the use thereof.

In recent decades, major efforts have been undertaken to increase the hardness and the abrasion resistance of plastic-based dental materials. In this connection, di-or polyfunctional (meth)acrylate monomers (e.g., UDMA or Bis-GMA) have in particular been filled with inorganic fillers. Di-and polyfunctional (meth)acrylate monomers are to be understood as meaning monomers which have two or more polymerizable (meth)acrylate groups in the molecule. These are also subsequently described as crosslinking agents. Use is usually made, in dental materials, of mixtures of mono-and polyfunctional monomers having polymerizable groups, predominantly based on (meth)acrylate.

The attempts have gone so far that, for example, with direct filling materials degrees of filling with a proportion of inorganic filler of up to more than 90% by weight have been achieved. However, the high filler content leads to the result that the composites can no longer be optimally polished to a high finish or it was necessary to use mixtures of different fillers. This makes necessary a sometimes quite complicated balancing of the different fillers with regard to the chemical composition, the particle size and the particle size distribution, as also the surface treatment thereof. The surface roughness sometimes resulting already leads, by itself, to an increase in the susceptibility to plaque and discoloration. In addition, the junctions between the hard inorganic filler particles and the organic matrix can form microfissures by hydrolytic processes, in spite of a chemical surface modification (generally a silanization) of the filler particles. This furthermore can result in an increased susceptibility to plaque and discoloration. In addition to the physical influences, plastics formed from polyfunctional monomers have, in comparison with (meth)acrylate materials, a tendency towards increased deposition of plaque and an increased susceptibility to discoloration. Plaque is a supragingival tooth film which is deposited as a soft layer on exposed tooth surfaces and consists predominantly of food residues, saliva constituents and also bacteria and the metabolic products thereof. As first nucleus, *Streptococcus* sanguis attaches itself via lectins to the enamel cuticle. Extracellular polysaccharides formed by *Streptococcus mutans* increase the adhesion. In particular, Streptococci convert sugar to lactic acid and pyruvic acid, which demineralize the enamel.

EP 0 674 896 B1 describes a dental material comprising quaternary ammonium compounds with a germicidal bacteriostatic action.

WO 98/48766 describes dental materials comprising triclosan as antibacterial substance. However, it is a disadvantage that the triclosan is leached out, so that a long-term action is not retained.

WO 2004058193 describes a dental material with bacteriostatic and/or bactericidal substances. In this patent application, a description is given of active substances, e.g. taurolidine, which is inactive in the pH range from 6 to 7 and consequently is only activated by a change in the pH value as a result of the activity of the bacteria. Furthermore, a disadvantage of the dental materials described is that the use of the bactericidal additives can interfere with or lastingly change the natural bacterial medium in the mouth of the patient.

However, materials are also known in the dental field which do not have such a strong tendency towards depositions of plaque and discolorations as the composites described at the start. In this connection, they are, on the one hand, ceramic materials and, on the other hand, thermoplastics.

For thermoplastics, polymethyl methacrylate occupies an important role in dental applications. In this connection, PMMA is today used, because of the increased requirements with regard to abrasion resistance, first and foremost only as filler for prosthetic teeth and for denture base materials in complete replacements for teeth and also as temporary arrangement in the crown and bridge procedure. In this connection, uncrosslinked or weakly crosslinked PMMA particles are dissolved or swollen to a workable paste in monomethyl methacrylate comprising crosslinking agents and subsequently polymerized. These PMMA-based materials show very good resistance to plaque and discoloration. An additional thermoplastic with likewise very good resistance to discoloration and plaque is Teflon. However, the optical and physical properties of the material do not meet the requirements placed on a dental material. Ceramic materials, on the other hand, meet all requirements but are, partly due to the expensive processing and the high cost, used first and foremost for high-quality tooth replacement. Composites, on the other hand, represent an alternative which can easily be processed and which is of good value but still exhibit deficiencies which limit their usability in comparison with ceramic materials.

It is furthermore known that susceptibility to plaque and discoloration can be greatly reduced by the incorporation of particles of polymethyl methacrylate in monomer mixtures.

U.S. Pat. No. 4,946,901 describes (meth)acrylate-based precipitated fillers which have a particle size of approximately 5 to 100 µm and which can be used in filling materials, in teeth or also in facing materials.

U.S. Pat. No. 4,937,144 (=DE 3820497) furthermore describes strongly swelling fillers for dental applications which are precipitated from monomers which form crosslinkages, these monomers being in solution. Polymers with a degree of crosslinking of 50-100% by weight are described here, the mean particle size of which is 0.01-10 µm. The ratio of monomers which form crosslinkages to the swelling agent is given therein as 1:1 to 1:100. In principle, all plastics can be swollen. The degree of swelling of a plastic is in this connection dependent on the swelling agent used, the swelling temperature and the degree of crosslinking of the plastic.

EP 0 270 915 furthermore describes fillers for dental substances which are prepared by precipitation polymerization from di-or polyfunctional monomers which form crosslinkages of different (meth)acrylates. However, the accumulation of plaque or the susceptibility to discoloration cannot be reduced with these fillers.

All these fillers are prepared in such a way that a fine powder is obtained directly with the precipitation. However, with the incorporation thereof in composites, significant disadvantages arise with regard to the mechanical stability. It is furthermore disadvantageous for the filler particles thus obtained to exhibit a small particle size and accordingly to react in a very strongly thickening way.

DE 3000213 describes a process for the preparation of a crosslinked polymer with increase in the swelling rate. In this connection, a partially crosslinked copolymer is prepared and is subsequently modified for the increase in the swelling rate.

As an alternative form of the modification, a physical modification is carried out in the form of milling, high-energy radiation or mechanical structural disintegration. The second alternative form is the incorporation of a non-crosslinking monomer in the polymer structure. Afterwards, the non-crosslinking monomer is polymerized and a dry filler is obtained.

U.S. Pat. No. 2,013,295 describes the preparation of polymethyl methacrylate as filler for prosthetic materials. In this connection, an additive is added for the modifying of the polymethyl methacrylate. This can also be a liquid, e.g. triacetin, or also a plasticizer.

DE-OS 2000771 describes the preparation of hydrogels, which are prepared in a precipitation polymerization and then are processed to give various soft and flexible products. These gels, from partially crosslinked and partially uncrosslinked polymers with solvent components, are used as stable fillers in various applications.

It was henceforth the object of the present invention to make available a process for the preparation of composites by which polymerized materials, in particular polymethyl methacrylate, can better than hitherto be milled to the required particle size and incorporated in composites, without the mechanical properties being disadvantageously changed, in particular without embrittlement of the material occurring.

This object is achieved by a process for the preparation of composites which can be used in the dental field, in which
a) mono- and polyfunctional (meth)acrylates dissolved in a solvent are polymerized to give a polymer gel thoroughly swollen with the solvent,
b) the polymer gel is subjected to preliminary size reduction,
c) subsequently, a reactive gel is prepared by incorporating a polymerizable monomer or a mixture of polymerizable monomers in the polymer gel while simultaneously removing the solvent, and
d) a dental composite is prepared from the reactive gel thus obtained.

In the process according to the invention, first one or more monofunctional monomers are accordingly mixed with a crosslinking agent. Suitable monomers according to the invention are preferably methyl methacrylate. Additional monomethacrylate compounds, such as ethyl methacrylate or isobutyl methacrylate, are likewise suitable; however, the resistance to discoloration decreases with increasing molecular weight.

Suitable polyfunctional crosslinking agents are, for example, urethane dimethacrylate or addition products of methacrylic acid and bisphenol A diglycidyl ether (Bis-GMA). In this connection, short-chain dimethacrylates with a low molecular weight, such as, e.g., ethylene glycol dimethacrylate (MW=198), are not suitable since they result in embrittlement of the polymer.

The mono- and polyfunctional (meth)acrylates are dissolved in a solvent. Those which are suitable for this are preferably inert solvents, i.e. solvents which do not participate in the polymerization. Because of this, it should be guaranteed that the solvents are merely physically incorporated, without participating in the polymerization reaction. The solvents which can be used include, e.g., acetone, ethanol, hexane, toluene or ethyl acetate. The boiling point of the solvent should lie in the temperature range in which the catalyst (e.g., peroxides, peroxycarbonates or azo compounds) forms radicals for initiating the polymerization reaction.

The components mentioned are preferably used in the following quantitative proportions:
5 to 70% by weight of monofunctional monomers, preferably 10 to 50% by weight, particularly preferably 20 to 35% by weight
5 to 70% by weight of di- or polyfunctional monomers, preferably 10 to 50% by weight, particularly preferably 25% by weight
20 to 70% by weight of a solvent, preferably 30 to 60% by weight, particularly preferably 50% by weight,
the individual components each time adding up to 100% by weight.

It is particularly preferable according to the invention when the ratio of mono- and polyfunctional (meth)acrylates to solvent is from 1:3 to 1:0.75, preferably 1:2 to 1:0.9, very particularly preferably 1:1. The polymerization of the monomer mixture used is preferably carried out in the presence of a heat-curing catalyst. Suitable catalysts are in particular dilauroyl peroxide, dibenzoyl peroxide, cumene hydroperoxide, azobisisobutyronitrile, tert-butyl peroctoate or diisopropyl peroxydicarbonate.

The polymerization process is carried out in such a way that the mixture is heated at least up to the temperature for formation of the radical from the catalyst. The polymerization of the monomer mixture accordingly starts. It is particularly advantageous for this process to be carried out as "heating under reflux" in the vicinity of the boiling point of the solvent used. For example, when using acetone, a boiling point of approximately 56° C. is set for carrying out the process. In this connection, a polymer gel thoroughly swollen with the solvent is produced. The polymer gel produced in this way is easy to reduce in size.

Care is taken, in the choice of the solvent and the diluting of the reactive mixture, that the heat produced by the exothermic reaction can be removed. The structure of the polymer gel is weaker or stronger depending on the monomers and solvents used and also the mixing ratios thereof. The bigger the ratio of the polymerizable monomers to the solvent, the more solid the polymer gels become.

The polymer gel comprises the monomer/solvent mixture in a ratio of monomer mixture to solvent of 1:3 to 0.75, preferably 1:2 to 1:0.9, very particularly preferably 1:1.

After the polymerization of the monomers and the thorough swelling with the solvent, the polymer gel is conveyed to the next process stage, i.e. the preliminary size reduction. The preliminary size reduction of the polymer gel can take place in conventional devices. Standard chopping devices, e.g. Dirks mixer, 2- or 3-roll mills and similar devices, may be suitable, for example.

The preparation of the reactive gel takes place subsequent to the preliminary size reduction, i.e. an incorporation of a polymerizable monomer in the polymer gel still thoroughly swollen with the solvent. At the same time as the incorporation of a polymerizable monomer, the solvent is removed, i.e. the solvent is replaced by polymerizable monomer. As a result, a new gel is accordingly formed. This gel is described, in the context of the present description, as reactive gel.

Use may be made, for this, of devices known to a person skilled in the art. Preference is given, according to the invention, to the use of a 3-roll mill. Three-roll mills are homogenizing and size reducing units, such as those used in the paint and also cosmetics industry for the preparation of color pastes and creams. In this connection, the body of material is transported through three rolls which rotate countercurrentwise. In this connection, the polymer gel is reduced in size and the polymerizable monomer is incorporated for the preparation of the reactive gel. A very precise particle size reduction and dispersing can be achieved by adjusting the roll gap (e.g., Exact three-roll mill from EXACT Vertriebs GmbH, 22851 Norderstedt, Germany).

Suitable polymerizable monomers for incorporation in the polymer gel are, e.g., polymerizable matrix monomers, such as, e.g., urethane dimethacrylate (UDMA), addition products of methacrylic acid and bisphenol-A diglycidyl ethers (Bis-GMA), carbonate dimethacrylates, ethylene glycol dimethacrylates or epoxide resins. Silicone and polyester resins are likewise suitable.

In addition, it is also possible, according to the invention, for the polymer gel, which has been subjected to preliminary size reduction, to be processed as a precursor in highly concentrated form with monomers which form crosslinkages, to give prepastes which can subsequently be incorporated in composites. The polymer gels according to the invention can also be incorporated in monomethacrylates which can, for example, be used in solvent-free dental coating products as reactive diluent.

As a result, the incorporation of the polymer gels, which have been subjected to preliminary size reduction, in polymerizable monomers results in the production of a paste in which the initial polymer gel is swollen with the reactive monomer to give a reactive gel. That is to say, a gel is formed comprising a polymerized component (described as polymer gel in the context of the invention) and a non-polymerized component in the form of a polymerizable monomer. The modified gel (reactive gel) produced is reactive, in other words polymerizable.

Composites which can be used in the dental field can then be prepared from this paste. This is preferably carried out by mixing the reactive gel with a matrix monomer and, if appropriate, polymerization initiators. Use may be made, as matrix monomers, of urethane dimethacrylate (UDMA), addition products of methacrylic acid and bisphenol-A diglycidyl ethers (Bis-GMA), carbonate dimethacrylates, ethylene glycol dimethacrylates or epoxide resins. Silicone and polyester resins are likewise suitable.

Furthermore, additional inorganic fillers, for example $SiO_2$, glass fillers, prepolymers or organic fillers can be incorporated in the preparation of the composites. In this connection, the prepolymers can also comprise an inorganic filler. Use may likewise be made of inorganic fillers based on zirconium oxide or mixed oxides, such as silicon dioxide and aluminum oxide. Surface-treated nanoparticles can also be incorporated. In this connection, the inorganic fillers should specifically be surface-modified chemically using a functional silane in order to produce chemical bonding to the polymerizable monomer matrix. The degree of filling to be achieved depends on the amount of the swollen filler incorporated, on the viscosity of the composite monomer and on the particle size of the inorganic and organic fillers used.

The composites prepared according to the invention can be cured using all known polymerization methods. The appropriate working methods can be chosen depending on the catalyst system used or on the curing mechanism of the monomers used in the composite. Use may be made, e.g., of light-curing materials (photoinitiator), cold-curing materials (e.g., amine/peroxide) or heat-curing materials (e.g., peroxides) or cationically curable materials.

The reactive gels or composites prepared according to the process according to the invention can be used in the dental field in varied ways. Thus, they can, for example, be used for teeth, composite cements, filling composites, fissure sealants, characterizing colors for tooth surfaces, and the like.

The composites prepared according to the invention have significant advantages in comparison with the dental composites known hitherto. In particular, a clear reduction in the affinity for colorants can be noted, which results in clearly reduced surface discolorations of tooth restorations. In comparison with the prepolymers known hitherto, clearly finer particle sizes (smaller than 1 µm) can be achieved as well. The particles exhibit an irregular shape.

On the other hand, most commercially available polymethacrylates exist as spheres. However, spheres are not optimally suitable as filler because spherical filler particles are easily broken off from the surface as soon as, with grinding, the level falls below that of the midline of the particle.

The refractive index of pure polymethyl methacrylate is 1.49 and is accordingly highly suitable for use in dental composites. The refractive index can be adjusted and optimized by the choice of crosslinking agents with higher or lower refractive indices which are used according to the invention for the gel preparation. An additional advantage is that the products obtained from the reactive gels according to the invention are not brittle. In addition, high X-ray opacities can be obtained by the incorporation of iodinated aromatic (meth)acrylate crosslinking agents.

Furthermore, the matrix systems provided with the reactive gel prepared according to the invention can be strengthened and filled with additional inorganic fillers without any problems. Likewise, reactive gels swollen with the process according to the invention can be prepared on the exclusive basis of pure crosslinking monomers which can be used to reduce abrasion in polymethyl methacrylate systems.

In a further embodiment, the polymerization is carried out in such a way that a tack-free polymer gel is obtained.

The reactive gels can furthermore be used for silicone relining for prostheses for reducing susceptibility to plaque and discoloration. In this connection, the filler-comprising reactive gel can be directly prepared in a silicone and ground down or reduced in size on a three-roll mill.

Finally, the susceptibility to plaque and discoloration of dental solvent-free coatings can also be reduced by using the reactive gel. These coatings can be used as replacement polish, e.g. on crowns and bridges or complete replacements for teeth, and can thus noticeably reduce the cost for dental technicians.

The invention is more fully described below with reference to the examples, these examples not limiting the invention:

EXAMPLE 1

Microfilled Composite Systems

Stage 1: Swollen And Crosslinked PMMA (Polymer Gel)

| | |
|---|---|
| Methyl methacrylate | 100 g |
| UDMA 1 (MW 513) | 100 g |
| Acetone | 200 g |
| Dilauroyl peroxide | 2 g |

Step 2: Preliminary Size Reduction

The solvent-free polymer gel is reduced in size in a laboratory mixer and the dry residue or acetone content is subsequently determined: acetone content=42%

Stage 3: Incorporation In Composite Monomer

| | | |
|---|---|---|
| Composite monomer mixture | 42.5 g | 80% UDMA + 20% decanediol dimethacrylate |
| Swollen crosslinked polymer gel | 34.5 g | Acetone content 35% = 20 g dry weight |

The abovementioned mixture is homogenized on an Exact 80 E three-roll mill. The roll gap is uniformly 10 μm. After the homogenization, the remaining solvent (acetone) is removed under vacuum at 55° C.

Stage 4: Preparation of Composites

| | | |
|---|---|---|
| Composite monomer with polymer gel | 62.5 g | From stage 3 |
| Pyrogenic silica, silanized | 37.0 g | SiO$_2$, silanized |
| tert-Butyl peroctoate | 0.5 g | |
| Total | 100.0 g | |

The silica and the catalyst are incorporated in a laboratory kneader.

Breakdown of the Formulation

| | |
|---|---|
| Aliphatic DMA | 8.4 |
| UDMA 1 | 34.1 |
| Polymer gel according to the invention | 20.0 |
| Pyrogenic silica, silanized | 37.0 |
| tert-Butyl peroctoate | 0.5 |
| Total | 100.0 |

DMA Dimethacrylate (decanediol dimethacrylate)
UDMA 1 Adduct of TMDI (trimethylhexamethylene diisocyanate) and HEM (hydroxyethyl methacrylate)
UDMA 2 Urethane dimethacrylate adduct of TMXDI (1,3-bis(isocyanato-1-methylethyl) benzene) and HEMA

EXAMPLES

Test Composite 1:

| | |
|---|---|
| UDMA monomer (UDMA 2) | 34.1% by weight |
| Decanediol dimethacrylate | 8.4% by weight |
| Swollen crosslinked PMMA (polymer gel) | 20.0% by weight |
| Pyrogenic silica, silanized | 37.0% by weight |
| tert-Butyl peroctoate | 0.5% by weight |

Test Composite 2:

| | |
|---|---|
| UDMA monomer (UDMA 1) | 34.1% by weight |
| Decanediol dimethacrylate | 8.4% by weight |
| Swollen crosslinked PMMA (polymer gel) | 20.0% by weight |
| Pyrogenic silica, silanized | 37.0% by weight |
| tert-Butyl peroctoate | 0.5% by weight |

Both composites were polymerized for 20 minutes in an autoclave at 140° C. and in a nitrogen atmosphere at a pressure of 5 bar.

The following materials were used for the comparison of the composites according to the invention with comparable materials from the state of the art used for plastic teeth:

Conventional Composite:

| | |
|---|---|
| 60% by weight | UDMA 1 (with 1% catalyst) |
| 40% by weight | Pyrogenic silica |

Crosslinked PMMA
Standard Material For Prosthetic Teeth
Physical Values

| | Example 1 | Example 2 | Conventional composite | Crosslinked PMMA |
|---|---|---|---|---|
| Flexural strength (MPa) | 123 ± 7 | 128 ± 16 | 95 | 120 |
| E modulus (MPa) | 6087 ± 290 | 5550 ± 535 | 5100 | 3000 |
| Vickers hardness | 380 ± 2 | 370 ± 8 | 300 ± 9 | 190 ± 5 |
| Ball indentation hardness | 310 ± 3 | 302 ± 5 | 270 ± 4 | 170 ± 4 |

Determination of the Susceptibility To Discoloration:

In order to determine the susceptibility to discoloration of the abovementioned examples, test samples were incorporated in a colorant solution (0.01% aqueous safranin red solution) and the color value was determined.

Test Method

The reflux apparatus consisted of a 200 ml round-bottomed flask with a ground glass joint and an Allihn condenser. The abovementioned colorant solution (100 ml) and the test samples were introduced at ambient temperature and the solution was subsequently heated up and left refluxing for 16 hours.

The solution together with the test samples was then cooled down and the samples were removed from the flask, rinsed with cold faucet water and dried with a paper towel. The difference in the color values before and after storing in safranin solution was determined using a Minolta color spectrometer and compared:

Test Results

| | L* | a* | b* |
|---|---|---|---|
| Crosslinked PMMA | 0.82 | −0.12 | 0.08 |
| Conventional composite | −29.56 | 43.86 | 7.34 |
| Example 1 | −0.31 | 6.83 | 1.18 |
| Example 2 | −1.91 | 5.35 | −1.43 |

Results of the Discoloration Test

It can be seen, from the calorimetric data, that composites prepared according to the invention are clearly less susceptible to discolorations than conventional composites. Example 2 is prepared with the same monomer matrix as the conventional composite but nevertheless shows a greatly reduced colorant affinity.

FIG. 1 shows a graphic representation of the results shown in the table labeled Test Results setting forth the L*, a* and b* values. It illustrates that composites prepared according to the invention (examples 1 and 2) are clearly less susceptible to discolorations than conventional composites.

Determination of the Plaque Index:

In addition to the determination of the susceptibility to discoloration, the plaque susceptibility exhibited by a material can also be established by means of an in vivo test. For this, 3 small blocks with up to nine materials to be tested are each time incorporated in prostheses on the cheek side. Since plaque deposition differs from patient to patient and also according to the position in the mouth, a positive and a negative sample have to be incorporated in each block. Use is each time made, as reference materials, of a conventional composite as negative sample (gives a great deal of plaque) and of a crosslinked PMMA as positive sample (little susceptibility to plaque formation). After being worn for a time of preferably approximately one year, the materials are tested for attack by plaque. For this, the samples are prepared from the prosthesis and assessed by at least 3 people under a light microscope. From the positive and negative samples, the plaque index can be established via an index classification. If the entire surface of a sample is covered with plaque, the plaque index 5 results; if there is no plaque on the sample, the plaque index is 0. In addition, the plaque susceptibility of a patient can be determined via reference samples. Experience shows that a material with a plaque index of less than 1.5 exhibits very little affinity for plaque.

What is claimed is:

1. A process for the preparation of composites which can be used in the dental field, in which
   a) mono-or polyfunctional (meth) acrylate monomers dissolved in a solvent are polymerized to give a polymer gel thoroughly swollen with the solvent,
   b) the polymer gel produced is subjected to preliminary size reduction,
   c) subsequently, a reactive gel is prepared by incorporating a polymerizable monomer or a mixture of polymerizable monomers in the size reduced polymer gel while simultaneously removing the solvent,
   d) a dental composite is prepared from the reactive gel thus obtained, wherein the resulting particles exhibit an irregular shape; and
   e) wherein the polymer gel is and remains swollen during the entire process from its preparation up until its incorporation into the dental composite.

2. The process as claimed in claim 1, wherein, in stage a), methyl methacrylate, ethyl methacrylate, benzyl methacrylate, isobutyl methacrylate or other low molecular weight monomethacrylates are used as monomer.

3. The process according to claim 1, wherein, in stage a), polyfunctional monomers are used.

4. The process as claimed in claim 1, wherein, in stage a), a urethane dimethacrylate is used as crosslinking agent.

5. The process as claimed in claim 1, wherein, in stage a), the solvent is not involved in the polymerization reaction.

6. The process as claimed in claim 1, wherein use is made, as solvent, of acetone, ethanol, hexane, toluene, ethyl acetate or a mixture of one or more of these solvents.

7. The process as claimed in claim 1, wherein, in stage a), 5 to 70% by weight of monomers, 5 to 70% by weight of crosslinking agent and 30 to 70% by weight of solvent are used, the composition of the individual components in each case adding up to 100% by weight.

8. The process as claimed in claim 1, wherein the polymerization is carried out in the region of the boiling point of the solvent.

9. The process as claimed in claim 1, wherein the polymerization is carried out in the presence of a catalyst.

10. The process as claimed in claim 1, wherein lauroyl peroxide is used as catalyst.

11. The process as claimed in claim 1, wherein polymerization is carried out in such a way that a tack-free polymer gel is obtained.

12. The process as claimed in claim 1, wherein the preliminary size reduction is carried out in a chopping device.

13. The process as claimed in claim 1, wherein the ratio of monomers and crosslinking agents to solvents is from 1:3 to 1:0.75.

14. The process as claimed in claim 1, wherein use is made, as polymerizable monomer, of urethane dimethacrylate, Bis-GMA, carbonate dimethacrylates, ethylene glycol dimethacrylates or epoxide resins.

15. The process as claimed in claim 1, wherein the step of incorporation in a monomer of the polymer gel which has been subjected to preliminary size reduction is carried out in a three-roll mill.

16. The process as claimed in claim 1, wherein the polymer gel which has been subjected to preliminary size reduction is processed with short-chain crosslinking agents to give pre-pastes.

17. The process as claimed in claim 16, wherein the pre-pastes are incorporated in composites.

18. The process as claimed in claim 1, wherein, in stage d), inorganic or organic fillers are used for the preparation of the composites.

19. The process as claimed in claim 18, wherein $SiO_2$ or glass are used as inorganic fillers.

20. A method for preparing a dental composite, comprising the steps of:
   a) mono-and or polyfunctional (meth) acrylate monomers dissolved in a solvent are polymerized to give a polymer gel thoroughly swollen with the solvent,
   b) subjecting the polymer gel produced is subjected to preliminary size reduction,
   c) subsequently preparing a reactive gel by the polymer gel, subjected to preliminary size reduction, incorporating a polymerizable monomer or a mixture of polymerizable monomers in the polymer gel while simultaneously removing the solvent, and
   d) preparing the dental composite from the reactive gel thus obtained, wherein the resulting particles exhibit an irregular shape,
   e) wherein the polymer gel is and remains swollen during the entire process from its preparation up until its incorporation into the dental composite.

* * * * *